United States Patent [19]

Enomoto et al.

[11] Patent Number: 4,849,434

[45] Date of Patent: Jul. 18, 1989

[54] NOVEL THIAZOLIDIN-4-ONE DERIVATIVES AND ACID ADDITION SALTS THEROF

[75] Inventors: Masao Enomoto, Ibaraki; Masami Muraoka, Funabashi; Keiichi Ono, Sakai; Atsuyuki Kojima, Takarazuka; Toshio Atsumi, Kawanishi; Yoshihiro Komuro, Nishinomiya; Yuzuru Sanemitsu, Ashiya; Masato Mizutani, Toyonaka, all of Japan

[73] Assignees: Sumitomo Pharmaceuticals Company, Limited; Sumitomo Chemical Company, Limited, both of Osaka, Japan

[21] Appl. No.: 74,873

[22] Filed: Jul. 17, 1987

[30] Foreign Application Priority Data

Jul. 24, 1986 [JP] Japan .................. 61-174281

[51] Int. Cl.$^4$ .................. C07D 213/04; A61K 31/44
[52] U.S. Cl. .................. 514/342; 546/280
[58] Field of Search .................. 546/280; 514/342

[56] References Cited

U.S. PATENT DOCUMENTS 3,705,153 12/1972 Kaneko et al. .................. 546/280
4,017,628 4/1977 Nitidandhaprabhas et al. ... 514/342

FOREIGN PATENT DOCUMENTS 48-17276 5/1973 Japan .................. 546/280
55-55184 4/1980 Japan .................. 546/280
2031892 4/1980 United Kingdom .................. 546/280

OTHER PUBLICATIONS

J. Am. Chem. Soc., 75, 109–114 (1953).
J. Am. Chem. Soc., 76, 578–580 (1954).
J. Am. Chem. Soc., 70, 3436–3439 (1948).
J. Indian. Chem. Soc., vol. L IV, 1977, pp. 765–768.
J. Indian. Chem. Soc., vol. L III, 1976, pp. 595–597.
J. Indian. Chem. Soc., vol. L V, 1978, pp. 424–426.
J. Biol. Chem., 255, 5514–5516 (1980).

Primary Examiner—Mary C. Lee
Assistant Examiner—Zinna Northington
Attorney, Agent, or Firm—Stevens, Davis, Miller & Mosher

[57] ABSTRACT

A novel 2-pyridylthiazolidin-4-one derivative represented by the general formula

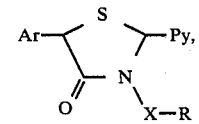

wherein Ar denotes an aryl group unsubstituted or substituted with a halogen atom or with a lower alkoxy group; X denotes a straight-chain or branched-chain lower alkylene group or a single bond; R denotes a hydrogen atom, lower alkyl, lower alkenyl, lower alkynyl, cycloalkyl, acyloxy, di(lower alkyl) amino, hydroxyl or aryl group, or denotes an aryl group substituted with a lower alkoxy group; and Py denotes a pyridyl group, and the acid addition salt thereof, which have an excellent platelet activating factor antagonsm.

14 Claims, No Drawings

NOVEL THIAZOLIDIN-4-ONE DERIVATIVES AND ACID ADDITION SALTS THEROF

FIELD OF THE INVENTION

This invention relates to novel 2-pyridylthiazolidin-4-one derivatives which show an excellent antagonism to the platelet activating factor (hereinafter abbreviated as PAF).

The platelet activating factor (PAF) is autacoid present in living body which has been recently identified as acetyl glyceryl ether phosphorylcholine (AGEPC), namely 1-o-hexadecyl/octadecyl-2-o-acetyl-sn-glyceryl-3-phosphorylcholine [Hanada, D. S. et al., J. Biol. Chem. 255, 5514 (1980)].

PAF exhibits various physiological activites which include, for example, platelet activation, blood pressure depression, smooth muscle contraction, neutrocyte-, monocyte- and macrophage-activation, increasing viscular permeability, and liver glycogen decomposition acceleration.

It is known that these physiological actions are related to many diseases, for example various kinds of inflammation, circulatory diseases, allergic diseases and gastrointestinal diseases. Accordingly, it is the course of nature that more and more scientists have come to focus their attention to work of searching PAF antagonists intended for preventing or curing these PAF-induced diseases.

However, although many compounds have been tested up to the present to treat or prevent the PAF-induced diseases, their effectiveness are not yet fully satisfactory.

On the other hand, a number of studies have been reported which relate to thiazolidin-4-one derivatives. For example, Surrey has studied the reaction of thioglycolic acid with Schiff base and reported a method of synthesizing thiazolidin-4-one derivatives; these compounds are known to show an anticonvulsant activity [J. Am. Chem. Soc., 70, 3436–3439 (1948)]. Pennington et al. have reported a method of synthesizing 2-substituted thiazolidin-4-one derivatives and that these derivatives have a antitubercular activity in in vitro experiments [J. Am. Chem. Soc., 75, 109–114 (1953)].

Surrey et al. have reported a method of synthesizing a certain kind of 2-arylthiazolidin-4-one derivatives and that they have an amoebacidal activity (against *Endamoeba criceti*) [J. Am. Chem. Soc., 76, 578–580 (1954)].

Singh has reported methods of synthesis for a number of 5-methyl-3-aryl-2-aryliminothiazolidin-4-one derivatives and described that they show a fungicidal activity on *Alternaria solani* used as the test microorganism [J. Indian Chem. Soc., 595–597 (1976)]. Japanese Patent Application Kokoku (Post-Exam. Publn.) No. 17276/73 discloses their suppressive effect on the central nervous system. U.S. Pat. No. 4,017,628 (1977) discloses a method of treating the itch of domestic animals using a 2-pyridyl-substituted thiazolidin-4-one derivative. P. B. Patel et al. have reported that 2-aryl-3-aryloxyethyl-thiazolidin-4-one derivatives show an antiinflammatory action [J. Indian Chem. Soc., 54 (8), 765–768 (1977)]. Further, Jadhav et al. have reported a method of synthesizing a certain kind of 2-methyl-(2-hydroxy-4,5-dimethylphenyl)-3-arylthiazolidin-4-one derivatives and that they show a germicidal activity on some kind of fungi (*Helmy nthosporium appatarnae*) [J. Indian Chem. Soc., 424 –426 (1978)]. Further, Japanese Patent Application Kokai (Laid-Open) No. 55,184/80 discloses that they show a germicidal action for plants and a controlling action for land and aquatic plants. Thus, not a few of the thiazolidin-4-one derivatives show an excellent pharmacological action.

SUMMARY OF THE INVENTION

After extensive studies under such circumstances, the present inventors have found that 2-pyridylthiazolidin-4-one derivatives represented by the general formula [I]

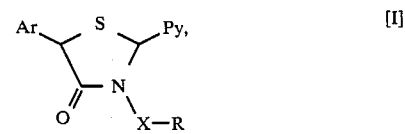

wherein Ar denotes an aryl group unsubstituted or substituted with one or more halogen atoms or with one or more lower alkyloxy groups; X denotes a straight-chain or branched-chain lower alkylene group or a single bond; R denotes a hydrogen atom, lower alkyl, lower alkenyl, lower alkynyl, cycloalkyl, acyloxy, di(-lower alkyl) amino, hydroxy or aryl group, or denotes an aryl group substituted with one or more lower alkyloxy group; and Py denotes a pyridyl group, and the acid addition salts thereof show a selective PAF-antagonism and are very useful as a preventive and curative agent for PAF-induced diseases including, for example, various kinds of inflammation, circulatory diseases, allergic diseases, and gastrointestinal ulceration, and thus accomplished this invention.

DESCRIPTION OF THE PREFERRED EMBODIMENT

The compounds of this invention will now be described in detail below.

In this invention, the lower alkyl groups include, for example, $C_{1-4}$ alkyl groups such as methyl, ethyl, n-propyl, isopropyl, n-butyl, isobutyl, sec-butyl and tert-butyl; examples of the lower alkoxy groups include $C_{1-4}$ alkoxy groups such as methoxy, ethoxy, n-propoxy, isopropoxy, n-butoxy, isobutoxy, sec-butyoxy, and tert-butoxy; those of the aryl groups include phenyl and naphthyl; those of the lower alkylene groups include $C_{1-4}$ alkylene groups such as methylene, ethylene, propylene, trimethylene, tetramethylene, and 1-methyltrimethylene; those of the lower alkenyl groups include $C_{3-4}$ alkenyl groups such as allyl and butenyl; those of the lower alkynyl groups include $C_{3-4}$ alkynyl groups such as propargyl; those of the cycloalkyl groups include $C_{3-7}$ cycloalkyl groups such as cyclopropyl, cyclopentyl, and cyclohexyl; those of the acyloxy groups include $C_{1-4}$ alkanoyloxy groups such as acetyloxy, or aroyloxy groups such as benzoyl; those of the halogen atom include a fluorine, chlorine, and bromine atoms; and those of the di(lower alkyl) amino groups include di($C_{1-4}$ alkyl) amino groups such as dimethyl amino, diethyl amino, dipropyl amino. The "substituted aryl group" means an aryl group substituted with one or more substituents, said substituents being as mentioned above.

The pyridyl group denoted by Py may be bonded to the 2-position of the thiazolidin-4-one ring at any of the 2-, 3- and 4-position of the pyridine ring.

The salts of the thiazolidin-4-one derivatives represented by the general formula [I] may be any one of those pharmaceutically acceptable salts and include, the salts of inorganic and organic acids, e.g. the salts of mineral acids such as hydrochloric acid, hydrobromic acid, sulfuric acid, and phosphoric acid; the salts of organic carboxylic acids such as formic acid, acetic acid, fumaric acid, maleic acid, malic acid, tartaric acid, and aspartic acid; and the salts of sulfonic acids such as methanesulfonic acid, benzenesulfonic acid, toluenesulfonic acid, hydroxybenzenesulfonic acid, dihydroxybenzenesulfonic acid, and naphthalenesulfonic acid.

The compounds of this invention include their optical isomers, geometrical isomers and tautomers, and further all of the hydrates and the crysal forms therof.

The thiazolidin-4-one derivatives represented by the general formula [I] can be prepared, for example, by the following methods.

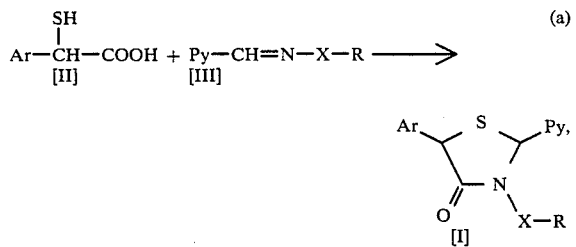

wherein Ar, Py, X and R are as defined above.

Thus, they can be prepared by subjecting the compounds [II] and [III] to ring closure in an organic solvent. The organic solvent may be a common inert solvent such as benzene, toluene, xylene, dichloromethane, 1,2-dichloroethane, chloroform, and tetrahydrofuran. The reaction can be carried out at a temperature from 20° C. to the reflux temperature. It is preferable to conduct it at the reflux temperature while azeotropically dehydrating to promote the reaction.

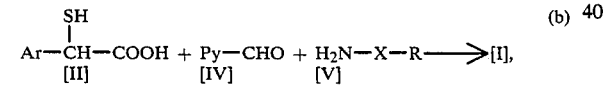

wherein Ar, Py, X and R are as defined above.

The compound [I] can also be obtained by allowing the compounds [III], [IV] and [V] to react in an organic solvent.

The organic solvent to be used may be a common inert solvent such as benzene, toluene, xylene, dichloromethane, 1,2-dichloroethane, chloroform, and tetrahydrofuran. The reaction can be carried out at a temperature from 20° C. to the reflux temperature, but preferably at the reflux temperature with azeotropically dehydrating.

These starting compounds are well-known or can be prepared by known methods. For example, the compounds represented by the formulas [II] and [III] could be obtained by the following methods, as described later in Reference Examples.

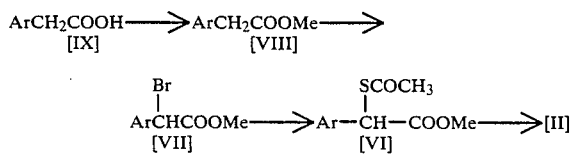

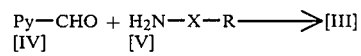

wherein Ar, Py, X and R are as defined above.

Thus, the starting compound [IX] was esterified according to the method described in Shin Jikken Kagaku Koza (A New Course of Experimental Chemistry), Vol. 14, p. 1002, to give an ester [VIII], which was then halogenated according to the method described in Shin Jikken Kagaku Koza, Vol. 14, p. 339, to give a brominated compound [VII]. The compound [VII] was further converted to a thiol ester compound [VI] according to the method described in Shin Jikken Kagaku Koza, Vol. 14, p. 1712, and then the compound [VI] was hydrolyzed with a base such as sodium hydroxide or potassium hydroxide in a water-alcohol mixed solvent, to give a mercaptan derivative [II].

The Schiff base compound [III] was obtained by subjecting an aldehyde [IV] and a primary amine [V] to dehydration condensation according to the method described in Shin Jikken Kagaku Koza, Vol. 14, p. 1410.

When the compounds of this invention represented by the general formula [I] mentioned above and their salts are used as a medicinal agents, they can be administered orally or parenterally. Thus, they can be administered orally in a conventionally used dosage form such as tablets, capsules, sirup, suspension and solution; or they can be made up into liquid preparations incuding their solution, emulsion and suspension and administered parenterally as injections. Further, they can be administered rectally in the form of suppositories, and also administered in the form of inhalation spray or endermic agents.

The pharmaceutical preparations of suitable dosage forms mentioned above may be prepared by compounding the active compound with conventional acceptable carriers, excipients, binders, stabilizers etc. For use in the form of injections, acceptable buffers, solubilizing aids, isotonificating agents, etc. may be added thereto.

Although the dose and the frequency of administration vary depending on the conditions, age, and weight of the patient, the dosage form, and other factors, a normal dose is about 1 to 5,000 mg, preferably 10 to 300 mg, in single or divided doses, per day for an adult.

EFFECT OF THE INVENTION

It has been revealed that the compound [I] of this invention shows a pharmacological action desirable as a curative agent for PAF-induced diseases. Namely, the compound [I] of this invention exhibits a powerful and selective PAF antagonism. The pharmacological effect of the compound of this invention will be described in detail below.

Inhibition of PAF-induced platelet aggregation in vitro test

The inhibition of PAF-induced platelet aggregation was examined by use of a platelet-rich plasma [PRP] of a rabbit according to the method of Mustard et al. [J. F. Mustard et al., J. Lab. Clin. Med., 64, 548 (1964)], which is an improved version of the method of Born [G. V. R. Born, J. Physiol., London, 162, 67 (1962)]. Thus, 80 to 100 ml of blood per animal was collected from the carotid artery of a Japanese white crossbred male rabbit without anesthesia into a polyethylene vessel in which 1/10 the volume of a 3.8% sodium citrate solution had been placed beforehand. A portion (about 3 ml) of the blood thus collected was subjected to high speed centrifugation (11,000 rpm, 60 seconds) to obtain a platelet-poor plasma (PPP) as supernatant. The remainder of the blood was subjected to low speed centrifugation (1,000 rpm, 10 minutes) to obtain a platelet-rich plasma (PRP) as supernatant.

The platelet aggregation was evaluated by nephelometry, the determination being made with PRP stirred at 1,000 rpm at 37° C. by use of an aggregater (Hematracer, Niko Bioscience Co.). The platelet aggregation activity was expressed in terms of the percent of light transmission, that of PRP being taken as 0% and that of PPP being taken as 100%. A 0.2 ml portion of PRP was placed in a glass cuvette containing a silicone-treated iron stirring rod, and 2 $\mu$l of dimethyl sulfoxide was added thereto. After 2 minutes, a PAF solution in 0.25% BSA physiological saline was added thereto to give a final concentration of PAF of 0.005 $\mu$g/$\mu$l and the maximum aggregation was determined. To examine the inhibitory activity of test compounds for the platelet aggregation caused by PAF, 2 $\mu$l of a test compound dissolved in dimethyl sulfoxide was added in place of dimethyl sulfoxide described above. The PAF inhibitory rate of a test compound was calculated according to the following equation:

$$\text{Inhibitory rate (\%)} = \left(1 - \frac{\text{Max. aggregation in test compound addition}}{\text{Max. aggregation in dimethyl sulfoxide addition}}\right) \times 100$$

The results thus obtained are shown in Table 1.

TABLE 1

| Inhibition of rabbit platelet aggregation caused by PAF | |
|---|---|
| Test compound (Example No.) | Specific activity relative to the activity of the compound of Example 1 |
| 1 | 1 |
| 4 | 1.3 |
| 5 | 0.9 |
| 11 | 0.7 |
| 13 | 2.3 |
| 14 | 1.4 |
| 15 | 0.5 |
| 17 | 1.0 |
| 19 | 1.2 |
| 21 | 2.2 |
| 27 | 0.6 |
| 32 | 1.8 |

The IC$_{50}$ of the compound of Example 1 was 5.0 $\mu$g/ml.

The inhibitory rate for blood pressure depression caused by PAF was calculated according to the follow equation:

$$\text{Inhibitory rate (\%)} = \left(1 - \frac{\text{Max. depression in administration of compound of Example 1}}{\text{Max. depression in control test}}\right) \times 100$$

Results:

Experiment 1  Inhibitory rate: 57%
Experiment 2  Inhibitory rate: 53%

Inhibition of pressure depression caused by PAF, in vivo test (Blood pressure determination method)

(1) A rat was anesthetized with urethane (6.25 mg/kg intravenous injection) and cannulated through the carotid artery and the jugular vein. The carotid artery cannula was connected to a hemomanometer transducer to determine the blood pressure. The compound of Example 1 was suspended in 10% Nikkol ® liquid to a concentration of 30 mg/ml, and 1 ml/kg of the resulting suspension was administered through the jugular vein cannula. After 5 minutes, 1 ml of a 0.1 $\mu$g/ml PAF solution was administered through the jugular vein cannula and then the maximum blood pressure depression was determined. For a control test, the vehicle (10% Nikkol ® liquid) was administered in place of the compound of Example 1.

(2) The compound of Example 1 was suspended in a 0.5% methylcellulose solution to a concentration of 50 mg/ml, and 1 ml/kg of the resulting suspension was orally administered to a rat. After 30 minutes from the administration, the rat was anesthetized with urethane (6.25 mg/kg intravenous injection) and cannulated through the carotid artery and the jugular vein. The carotid artery cannula was used for blood pressure determination and the jugular vein cannula for PAF intravenous injection. After 60 minutes from the administration of the medicine, 1 ml of a 0.1 $\mu$g/ml PAF solution was administered and then the maximum blood pressure depression was determined. For a control test, the vehicle (10% Nikkol ® liquid) was administered in place of the compound of Example 1.

Inhibition of platelet aggregation, outside-living-body test

The test compound was intravenously administered (30 mg/kg) to a rabbit or orally administered (50 mg/kg) to a guinea pig. Blood samples were collected, and the extent of platelet aggregation caused by $10^{-12}$–$10^{-6}$M of PAF was examined. The results are shown in Table 2. The numerical values in the Table show the PAF concentrations (EC$_{50}$ nM) necessary for causing an aggregation corresponding to 50% of the maximum PAF reaction.

TABLE 2

| The change with time of inhibitory effect EC$_{50}$ value, of the compound of Example 1 on platelet aggregation caused by PAF | | | | | | |
|---|---|---|---|---|---|---|
| | | Time elapsed after administration of compound of Example 1 (hr) | | | | |
| Animal | Administration route and dose | 0 | 0.5 | 1 | 2 | 4 |
| Rabbit | Intravenous administration, 30 mg/kg | 6.2 | 26 | 20 | 16 | 14 |
| Guinea pig | Oral administration, 50 mg/kg | 0.23 | 10 | 17 | 3 | 1 |

As stated in the foregoing, the compound [I] of this invention shows a powerful and highly selective PAF antagonism. This antagonism has been confirmed not only in in vitro test but also in outside-living-body test as well as in in vivo test. Further, the compound [I] of this invention shows a prolonged duration of action in living body which could not be found in prior art compounds. Accordingly, the compound [I] of this invention is very useful as a preventive and curative agent for PAF-induced diseases, for example various kinds of inflamation such as nephritis of rheumatism, circulatory diseases such as DIC* or endotoxin shock, allergic diseases such as astma and gastrointestinal ulceration such as gastric ulcer.

*DIC (disseminated intervascular coagulation)

This invention is further described in detail below by way of Examples and Referential Examples, but it is in no way limited thereto.

REFERENTIAL EXAMPLE 1

Methyl (4-chlorophenyl)acetate

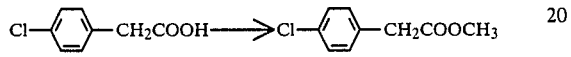

To a solution of 100 g (0.59 mole) of 4-chlorophenylacetic acid in 165 ml of 1,2-dichloroethane and 96 ml (2.4 moles) of methanol was added 2.75 ml of concentrated sulfuric acid, and the mixture was refluxed for 6 hours. It was then cooled, poured into an aqueous sodium bicarbonate solution and stirred. The organic layer was separated, dried over anhydrous sodium sulfate, filtered, and the filtrate was evaporated to dryness to give 102 g (94% yield) of methyl (4-chlorophenyl)acetate.

NMR (CDCl$_3$) δ ppm; 3.60 (2H, s), 3.70 (3H, s), 7.15–7.35 (4H, s)

REFERENTIAL EXAMPLE 2

Methyl (4-chlorophenyl)bromoacetate

To a solution of 102 g (0.55 mole) of methyl (4-chlorophenyl)acetate in 100 ml of carbon tetrachloride was added 97.9 g (0.55 mole) of N-bromosuccinimide. The resulting mixture was refluxed and irradiated with a 500 W bromo lamp for 5 hours. It was then cooled, filtered, and the filtrate was evaporated to dryness to give 150 g (103% yield) of methyl (4-chlorophenyl)-bromoacetate.

NMR (CDCl$_3$) δ ppm; 3.79 (3H, s), 5.31 (1H, s), 7.3–7.7 (4H, s)

REFERENTIAL EXAMPLE 3

Methyl α-(4-chlorophenyl)-α-acetylthioacetate

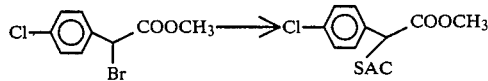

Under nitrogen atmosphere, 300 ml of dry dimethylformamide was added to 22.0 g (0.55 mole) of a 60% oily suspension of sodium hydride.

To the above mixture was added dropwise 46.0 g (0.61 mole) of thioacetic acid at 0° to 10° C. After the dropwise addition, the resulting mixture was maintained at 0° to 10° C. for one hour. Then, a solution of 150 g (0.55 mole) of methyl (4-chlorophenyl)bromoacetate in 200 ml of dry dimethylformamide was added dropwise at 0° to 10° C. thereto. Thereafter, the reaction mixture was kept at the same temperature for one hour.

The reaction mixture was poured into a 10% aqueous sodium chloride solution and extracted twice with benzene. The organic layer was washed with a 5% aqueous sodium bicarbonate solution, then twice with a 10% aqueous sodium chloride solution, dried over anhydrous sodium sulfate, filtered, and the filtrate was concentrated. The residue thus obtained was purified by silica gel chromatography (5% ethyl acetate-hexane) to give 128.0 g (95% yield) of methyl α-(4-chlorophenyl)-α-acetylthioacetate.

NMR (CDCl$_3$) δ ppm; 2.35 (3H, s), 3.74 (3H, s), 5.28 (1H, s), 7.25–7.40 (4H, m)

REFERENTIAL EXAMPLE 4

α-(4-Chlorophenyl)-α-mercaptoacetic acid

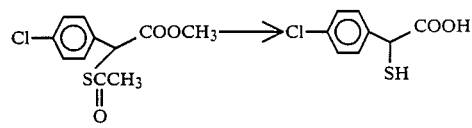

One hundred grams (0.39 mole) of methyl α-(4-chlorophenyl)-α-acetylthioacetate was dissolved in 350 ml of methanol. Then, a solution of 62.4 g (1.56 moles) of sodium hydroxide in 150 ml of water was added thereto, and the mixture was refluxed for 5 hours. After cooled, the reaction mixture was poured into a 10% aqueous sodium chloride solution and washed twice with hexane. The aqueous layer was adjusted to a pH of 1 to 2 with concentrated hydrochloric acid, and extracted twice with benzene. The organic layer was washed with a 10% aqueous sodium chloride solution, dried over anhhdrous sodium sulfate, and evaporated to dryness to give 68 g (86.8% yield) of α-(4-chlorophenyl)-α-mercaptoacetic acid.

NMR (CDCl$_3$) δ ppm; 2.62 (1H, d, J=7.6 Hz), 4.67 (1H, d, J=7.6 Hz), 7.3–7.45 (4H, s)

REFERENTIAL EXAMPLE 5

N-Nicotinylidenemethylamine

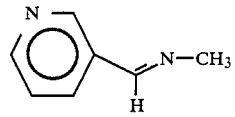

To a solution of 10.7 g (0.1 mole) of nicotinic aldehyde in 100 ml of toluene was added 233 g (0.3 mole) of a 40% aqueous methylamine solution, and the mixture was subjected to azeotropic dehydration for 3 hours. The reaction liquid was concentrated under reduced pressure to give 11.7 g of N-nicotinylidenemethylamine.

NMR (CDCl$_3$) δ ppm; 3.53 (3H, d, J=1.7 Hz), 7.3–8.85 (5H, m)

EXAMPLE 1

Synthesis of 5-(4-chlorophenyl)-3-methyl-2-(3-pyridyl)thiazolidin-4-one

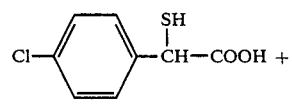

-continued

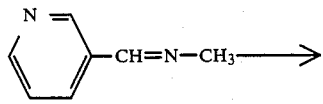

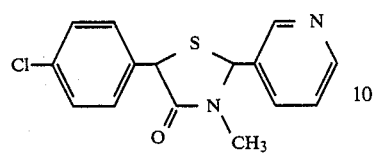

A 10.0 g (0.049 mole) portion of α-(4-chlorophenyl)-α-mercaptoacetic acid prepared in Referential Example 4 and 5.88 g (0.049 mole) of N-nicotinylidenemethylamine prepared in Referential Example 5 were dissolved in 100 ml of toluene, and the solution was subjected to azeotropic dehydration for 2 hours. The reaction mixture was cooled, washed with a 5% aqueous sodium bicarbonate solution, dried over anhydrous sodium sulfate, filtered, and the filtrate was concentrated under reduced pressure. The residue thus obtained was purified by silica gel chromatography (5% acetone-chloroform) and recrystallized from ether to give 13.5 g (90.0% yield) of 5-(4-chlorophenyl)-3-methyl-2-(3-pyridyl)thiazolidin-4-one, m.p. 100° to 101.5° C. (uncorrected).

EXAMPLE 2

Three grams of 5-(4-chlorophenyl)-3-methyl-2-(3-pyridyl)thiazolidin-4-one obtained in Example 1 was purified by liquid chromatography [Lichroprep® Si-60 (40-63 μm), mobile phase: ethanol-hexane=1:9] to obtain the isomer I and the isomer II.

M.p. (isomer I): 140°-140.5° C. (uncorrected)
M.p. (isomer II): 120°-120.5° C. (uncorrected)

EXAMPLE 3

5-(4-Chlorophenyl)-3-methyl-2-(3-pyridyl)thiazolidin-4-one

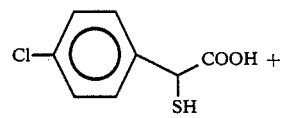

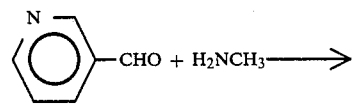

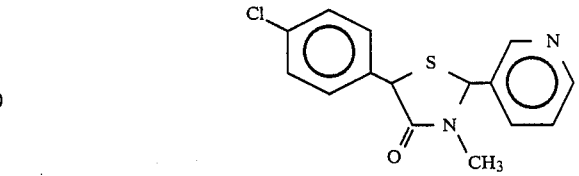

To 50 ml of toluene were added 5.0 g (0.025 mole) of α-(4-chlorophenyl)-α-mercaptoacetic acid prepared in Referential Example 4, 2.64 g (0.025 mole) of nicotinic aldehyde and 5.75 g (0.074 mole) of a 40% aqueous methylamine solution, and the mixture was subjected to azeotropic dehydration for 3 hours. The reaction mixture was cooled, and concentrated under reduced pressure. The residue obtained was purified by silica gel chromatography (5% acetone-chloroform) and recrystallized from ether to give 6.59 g (87.6% yield of 5-(4-chlorophenyl)-3-methyl-2-(3-pyridyl)-thiazolidin-4-one, m.p. 100° to 101.5° C. (uncorrected).

In the same manner as in Example 1 to 3, compounds of Examples 4 to 35 were obtained, which are enumerated in Table 3.

TABLE 3

| Example | Structure | NMR (CDCl₃) M.p. or δ ppm | IR cm⁻¹ |
|---|---|---|---|
| 4 | 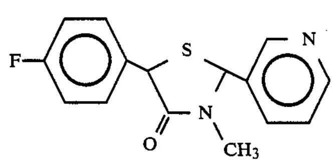 | 2.79(2H, s) 2.81(1H, s) 5.08(0.7H, s) 5.15(0.3H, d, J=1.9Hz) 5.60(0.7H, s) 5.69(0.3H, d, J=1.9Hz) | (CHCl₃): 1680, 1604, 1577, 1500, 1389, 1303, 1152, 1092 |
| 5 | 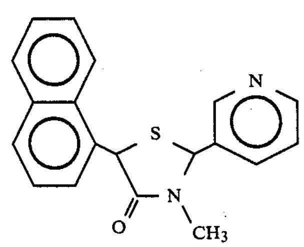 | M.p. 134–137° C. | nujol: 1692, 1584, 1020, 790 |

TABLE 3-continued

| Example | Structure | NMR (CDCl₃) M.p. or δ ppm | IR cm⁻¹ |
|---|---|---|---|
| 6 | 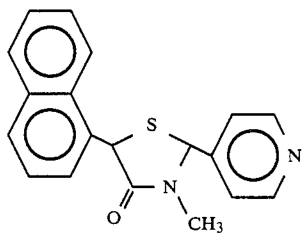 | M.p. 135.5–137.5° C. | nujol: 1665, 1597 |
| 7 | 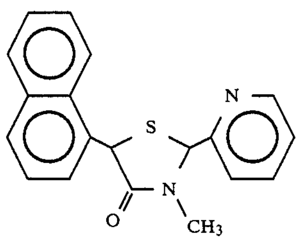 | M.p. 96.5–98.5° C. | nujol: 1670, 1590, 793, 711 |
| 8 | 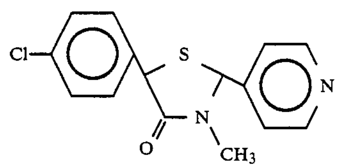 | M.p. 95.5–97° C. | nujol: 1675, 1595, 1086 |
| 9 | 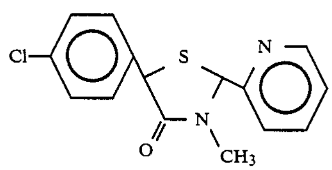 | M.p. 147.5–148.5° C. | nujol: 1690, 1588, 1084, 1012 |
| 10 | 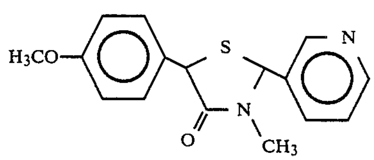 | M.p. 97–98° C. | nujol: 1681, 1668 (sh), 1513, 1036, 810 |
| 11 | 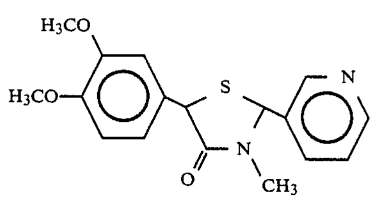 | 2.81(3H, s)<br>3.88(6H, s)<br>5.07(0.75H, s)<br>5.14(0.25H, d, J=1.7Hz)<br>5.60(0.75H, s) 5.68<br>(0.25H, d, J=1.7Hz) | neat; 1680, 1513 1260, 1139, 1025 |
| 12 | 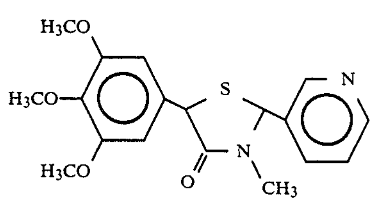 | M.p. 119–120.5° C. | nujol: 1664, 1591 1128, 1101 |

TABLE 3-continued

| Example | Structure | NMR (CDCl₃) M.p. or δ ppm | IR cm⁻¹ |
|---|---|---|---|
| 13 | (2,6-dichlorophenyl)-CH(S-CH(CH₃)-2-pyridyl)-C(O)-N(CH₃)H | M.p. 113.5–115° C. | nujol; 1690, 1578 |
| 14 | phenyl-CH(S-CH(CH₃)-2-pyridyl)-C(O)-N(CH₃)H | M.p. 148–150° C. | (CHCl₃): 1683, 1595, 1581, 1390, 1309, 1100 |
| 15 | (4-Cl-phenyl)-CH(S-CH(CH₃)-2-pyridyl)-C(O)-N(CH₂CH₃)H | 1.0–1.1(3H, m), 2.7–2.95 (1H, m), 3.65–3.9(1H, m) 5.06(0.5H, s), 5.12(0.5H, d, J=1.8Hz), 5.74(0.5H, s), 5.81(0.5H, d, J=1.8Hz) | (CHCl₃): 2970, 1590, 1578, 1488, 1087, 1010 |
| 16 Rf large | (4-Cl-phenyl)-CH(S-CH(CH₃)-2-pyridyl)-C(O)-N(CH₂CH=CH₂)H | 3.21(1H, dd, J=8.1, 15.1Hz), 4.4–4.5(1H, m) 5.1(1H, s), 4.9–5.3(2H, m), 5.71(1H, s) 5.6–5.8 (1H, m) | (CHCl₃): 1690, 1590, 1578, 1496, 1401, 1306, 1089, 1011 |
| 17 Rf small | (4-Cl-phenyl)-CH(S-CH(CH₃)-2-pyridyl)-C(O)-N(CH₂CH=CH₂)H | 3.16(1H, dd, J=7.9, 15.2Hz), 4.4–4.6(1H, m) 5.16(1H, d, J=1.8Hz), 5.0–5.3(2H, m), 5.55–5.75 (1H, m), 5.77(1H, d, J=1.8Hz) | (CHCl₃): 2955, 1685, 1590, 1577, 1485, 1403, 1090, 1010 |
| 18 Rf large | (4-Cl-phenyl)-CH(S-CH(CH₃)-2-pyridyl)-C(O)-N(CH₂C≡CH)H | 2.29(1H, t, J=2.6Hz) 3.54(1H, dd, J=2.6, 7.5Hz), 4.69(1H, dd J=2.6, 7.5Hz), 5.10 (1H, s), 5.91(1H, s) | (CHCl₃): 3300, 1690, 1591, 1577, 1487, 1400, 1352, 1088 |
| 19 Rf small | (4-Cl-phenyl)-CH(S-CH(CH₃)-2-pyridyl)-C(O)-N(CH₂C≡CH)H | 2.31(1H, t, J=2.6Hz) 3.33(1H, dd, J=2.6, 7.5Hz), 4.70(1H, dd J=2.6, 7.5Hz), 5.15 (1H, d), J=2.0Hz), 6.01 (1H, d, J=2.0Hz) | (CHCl₃); 3305, 1692, 1594, 1580, 1490, 1406, 1193 |
| 20 Rf large | (4-Cl-phenyl)-CH(S-CH(CH₃)-2-pyridyl)-C(O)-N(CH₂-(3,4-dimethoxyphenyl))H | 2.6–3.05(3H, m), 3.84(3H, s), 3.88 (3H, s), 3.8–4.0(1H, m), 5.02(1H, s), 5.31 (1H, s) | (CHCl₃): 2930, 2835, 1675, 1589, 1573, 1484, 1460, 1145, 1085 |

TABLE 3-continued
| Example | Structure | NMR (CDCl₃) M.p. or δ ppm | IR cm⁻¹ |
|---|---|---|---|
| 21 | 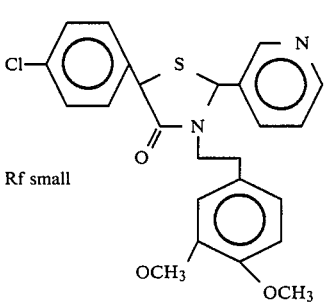 Rf small | 2.6–3.0(3H, m), 3.78(3H, s), 3.90 (3H, s), 4.0–4.1(1H, m), 5.06(1H, d, J=1.7Hz), 5.42(1H, d, J=1.7Hz) | (CHCl₃); 2940, 2845, 1680, 1593, 1579, 1490, 1360, 1094 |
| 22 | 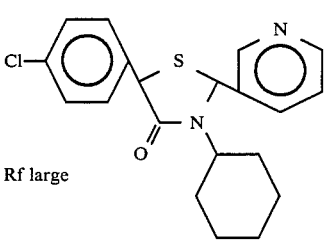 Rf large | 0.8–1.9(10H, m) 3.6–3.75(1H, m) 5.03(1H, s) 5.75(1H, s) | (CHCl₃); 2930, 2855, 1673, 1590, 1577, 1486, 1402, 1322 1089, 1010. |
| 23 | 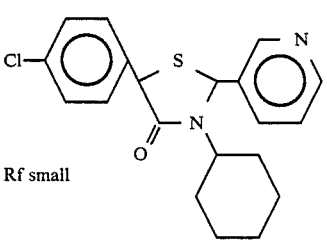 Rf small | 0.9–1.9(10H, m) 3.75–3.9(1H, m) 5.16(1H, d, J=1.7Hz) 5.78(1H, d, J=1.7Hz) | (CHCl₃); 2945, 2860, 1675, 1593, 1580, 1488, 1404, 1298 1091, 1015. |
| 24 | 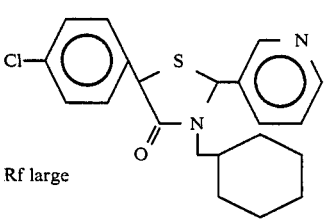 Rf large | 0.8–1.8(11H, m) 2.53(1H, dd, J=5.6 & 13.9Hz) 3.58(1H, dd J=8.5, 13.9Hz) 5.11(1H, s) 5.72(1H, s) | (CHCl₃); 2930, 2855, 1678, 1595, 1580, 1491, 1410, 1283 1018. |
| 25 | 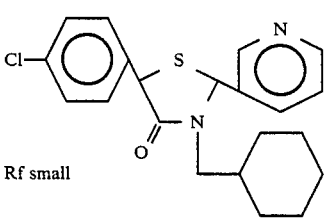 Rf small | 0.8–1.8(11H, m) 2.46(1H, dd, J=5.4 & 13.9Hz) 3.63(1H, dd J=5.4 & 8.8Hz) 5.13(1H, d, J=1.7Hz) 5.76(1H, d, J=1.7Hz) | (CHCl₃); 2930, 2855, 1678, 1590, 1578, 1487, 1279, 1090 1010. |
| 26 | 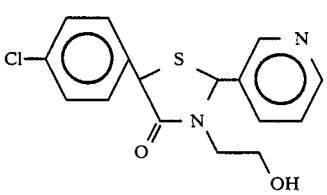 | 2.1–2.2(1H, m), 2.8–3.2 (1H, m), 3.6–4.0(3H, m) 5.1–5.2(1H, m), 5.94, (0.65Hs), 6.05 (0.35H, d, J=2.0Hz) | (CHCl₃); 1672, 1588, 1575, 1485, 1404, 1300, 1085, 1010. |

TABLE 3-continued
| Example | Structure | NMR (CDCl₃) M.p. or δ ppm | IR cm⁻¹ |
|---|---|---|---|
| 27 | 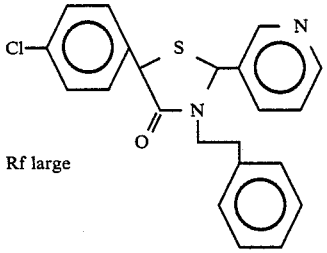 | 1.5–1.7(2H, m), 2.7–3.15 (2H, m), 3.4–3.85(3H, m) 5.12(0.5H, s), 5.18 (0.5H, d, J=2.0Hz), 5.73 (0.5H, s), 5.80(0.5H, d, J=2.0Hz) | (CHCl₃); 3450, 2940, 1665, 1592, 1577, 1489, 1409, 1348 1086, 1060. |
| 28 | 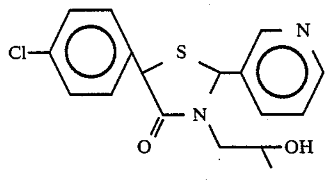 | 1.05–1.20(3H, m) 2.0–2.3 (1H, m), 2.6–2.85(1H, m), 3.5–4.2(3H, m), 5.1–5.2 (1H, m), 5.93(0.7H, s), 6.16(0.3H, d, J=2.0Hz) | (CHCl₃); 3420, 2965, 1675, 1592, 1578, 1487, 1407, 1090 1012. |
| 29 | Rf large | 2.6–3.05(3H, m) 3.8–4.0(1H, m) 5.04(1H, s) 5.28(1H, s) | (CHCl₃); 2930, 1680, 1591, 1578, 1490, 1407, 1359, 1089 1013. |
| 30 | 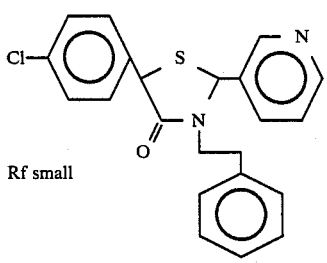 Rf small | 2.6–3.0(3H, m) 4.0–4.15(1H, m) 5.06(1H, d, J=1.8Hz) 5.34(1H, d, J=1.8Hz) | (CHCl₃); 2930, 1679, 1589, 1575, 1486, 1405, 1086, 1010. |
| 31 | 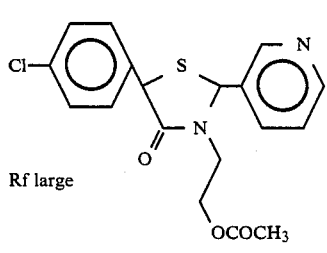 Rf large | 2.07(3H, s) 2.9–3.1(1H, m) 3.85–4.3(3H, m) 5.08(1H, s) 5.85(1H, s) | (CHCl₃); 2930, 1737, 1690, 1589, 1482, 1402, 1084. |
| 32 | 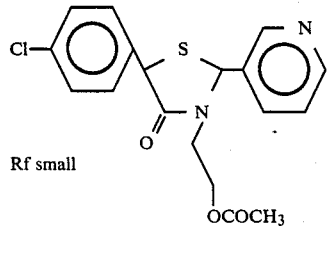 Rf small | 1.94(3H, s) 2.8–2.95(1H, m) 4.0–4.35(3H, m) 5.12(1H, d, J=1.7Hz) 5.93(1H, d, J=1.7Hz) | (CHCl₃); 2955, 1740, 1690, 1590, 1485, 1382, 1085. |

TABLE 3-continued

| Example | Structure | NMR (CDCl₃) M.p. or δ ppm | IR cm⁻¹ |
|---|---|---|---|
| 33 | Cl-C₆H₄-CH(S-)-C(=O)-N(-CH₂-pyridyl)(-CH₂CH₂CH₂OCOCH₃); Rf small | 1.7–2.0(2H, m) 2.00 (1.5H, s), 2.01(1.5Hs) 2.75–2.95(1H, m) 3.65–4.1 (3H, m), 5.07(0.5H, s), 5.12(0.5H, d, J=1.7Hz), 5.73(0.5H, s), 5.30 (0.5H, d, J=1.7Hz) | (CHCl₃); 2950, 1735, 1690, 1590, 1488, 1365, 1085. |
| 34 | Cl-C₆H₄-CH(S-)-C(=O)-N(-CH₂-pyridyl)(-CH₂CH(OCOCH₃)CH₃); Rf large | 1.15–1.20(3H, m) 2.04 (2.3H, s), 2.09(0.7H, s), 2.7–4.1(2H, m), 5.05–5.20 (2H, m), 5.78(0.23H, s), 5.95(0.77H, s) | (CHCl₃); 2955, 1730, 1684, 1586, 1482, 1401, 1083. |
| 35 | Cl-C₆H₄-CH(S-)-C(=O)-N(-CH₂-pyridyl)(-CH₂CH(OCOCH₃)CH₃); Rf small | 1.1–1.25(3H, m) 1.81(1.5H, s), 2.08 (1.5H, s), 2.6–4.1(2H, m), 5.0–5.2(2H, m) 5.85(0.5H, d, J=1.7Hz), 6.00(0.5H, d, J=1.7Hz) | (CHCl₃); 2960, 1734, 1685, 1588, 1485, 1370, 1085. |
| 36 | Cl-C₆H₄-CH(S-)-C(=O)-N(-CH₂-pyridyl)(-CH₂CH₂N(CH₃)₂); acetone: hexane: aqueous ammonia (50:50:3) Rf large | 2.18(6H, s), 3.8–3.95 (1H, m), 5.06(1H, d, J=1.9Hz), 6.11(1H, d, J=1.9Hz) | (CHCl₃); 1670, 1592, 1090, 1010. |
| 37 | Cl-C₆H₄-CH(S-)-C(=O)-N(-CH₂-pyridyl)(-CH₂CH₂N(CH₃)₂); acetone: hexane: aqueous ammonia (50:50:3) Rf small | 2.15(6H, s), 3.75–3.90 (1H, m), 5.10(1H, s), 5.98(1H, s) | (CHCl₃); 1683, 1590, 1090, 1010. |
| 38 | 2-Cl-C₆H₄-CH(S-)-C(=O)-N(CH₃)(-CH(pyridyl)-); Rf large | 140–141° C. | (nujol); 1663, 1586, 1255, 1020, 752. |

TABLE 3-continued

| Example | Structure | NMR (CDCl₃) M.p. or δ ppm | IR cm⁻¹ |
|---|---|---|---|
| 39 | Rf small | 140–141° C. | (nujol); 1665, 1579, 1248, 1020, 754. |
| 40 | Rf large | 84–87° C. | (nujol); 1690, 1587, 1301, 1102, 760 |
| 41 | Rf small | 138–140° C. | (nujol); 1662, 1580, 1440, 1255, 1103, 1000, 753. |

Note: "Large" or "small" Rfs in the second column of the Table refer to those in TLC (silica gel, developing solvent hexane : acetone = 6 : 4).
The melting point was uncorrected.

What is claimed is:

1. A 2-pyridylthiazolidin-4-one derivative represented by the formula

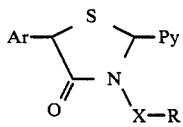

wherein
Ar is naphtyl or phenyl which is unsubstituted or substituted with one or more halogen atoms or with one or more C₁-C₄ alkoxy groups;
X is a straight or branched C₁-C₄ alkylene;
R is a hydrogen atom, C₁-C₄ alkyl, C₂-C₃ alkenyl, C₂-C₃ alkynyl, C₃-C₇ cycloalkyl, C₁-C₄ alkanoyloxy, di-C₁-C₄ alkyl-amino, hydroxy or phenylethyl which is unsubstituted or substituted with one or more C₁-C₄ alkoxy groups or X—R is C₃-C₇ cycloalkyl; and
Py is pyridyl;
and the acid addition salts thereof.

2. A compound according to claim 1 wherein Py is 3-pyridyl.

3. A compound according to claim 1 wherein Ar is a phenyl group unsubstituted or substituted with one or more halogen atoms or with one or more C₁-C₄ lower alkoxy groups.

4. A compound according to claim 1 wherein X—R is C₁-C₄ alkyl, C₃-C₄ alkenyl, C₃-C₄ alkynyl, phenylethyl which is unsubstituted or substituted with one or more C₁-C₄ alkoxy groups, C₂-C₄ alkanoyloxy-C₂-C₄ alkyl or di-C₁-C₄-alkylamino-C₁-C₄ alkyl.

5. A compound according to claim 2 wherein X—R is methyl, allyl, propargyl, acetoxyethyl, or dimethylaminoethyl.

6. A compound according to claim 2 wherein Ar is a phenyl group unsubstituted or substituted with one or more halogen atoms or with one or more C₁-C₄ alkoxy groups.

7. A compound according to claim 2 wherein X—R is C₁-C₄ alkyl, C₃-C₄ alkenyl, C₃-C₄ alkynyl, phenylethyl which is unsubstituted or substituted with one or more C₁-C₄ alkoxy groups, (C₂-C₄) alkanoyloxy (C₂-C₄)-alkyl, or di(C₁-C₄)-alkylamino (C₂-C₄) alkyl.

8. A compound according to claim 3 wherein X—R is C₁-C₄ alkyl, C₃-C₄ alkenyl, C₃-C₄ alkynyl, phenylethyl which is unsubstituted or substituted with one or more C₁-C₄ alkoxy groups, (C₂-C₄) alkanoyloxy (C₂-C₄)-alkyl, or di(C₁-C₄)-alkylamino (C₂-C₄) alkyl.

9. A compound according to claim 6 wherein X—R is C₁-C₄ alkyl, C₃-C₄ alkenyl, C₃-C₄ alkynyl, phenylethyl which is unsubstituted or substituted with one or more C₁-C₄ alkoxy groups, (C₂-C₄) alkanoyloxy (C₂-C₄)-alkyl, or di(C₁-C₄)- alkylamino (C₂-C₄) alkyl.

10. A compound according to claim 2, wherein X—R is phenylethyl or 3,4-dimethoxyphenylethyl.

11. A pharmaceutical composition for treatment of the disease caused by platelet activating factor, which comprises as an active ingredient a pharmaceutically effective amount of a compound as claimed in claim 1, and at least one pharmaceutically acceptable inert carrier or diluent.

12. A pharmaceutical composition for treatment of the disease caused by platelet activating factor, wherein the disease is inflammation, circulatory disease, gastrointestinal ulceration or allergy disease, which comprises as an active ingredient a pharmaceutically effective amount of a compound represented by the formula:

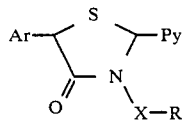

wherein Ar is a phenyl group unsubstituted or substituted with one or more halogen atoms or with one or more $C_1$–$C_4$ lower alkoxy groups, Py is 3-pyridyl, X—R is $C_1$–$C_4$ alkyl, $C_3$–$C_4$ alkenyl, $C_3$–$C_4$ alkynyl, phenylethyl which is unsubstituted or substituted with one or more $C_1$–$C_4$ alkoxy groups, ($C_2$–$C_4$) alkanonyloxy ($C_2$–$C_4$) alkyl, or di($C_1$–$C_4$) alkyl amino ($C_2$–$C_4$) alkyl and the acid addition salts thereof, and at least one pharmaceutically acceptable inert carrier or diluent.

13. A method for treatment of the disease caused by plate activating factor which comprises administering to a patient a pharmaceutically effective amount of a compound as claimed in claim 1, or a pharmaceutically acceptable salt thereof.

14. A method for treatment of the disease caused by platelet activating factor which comprises administering to a patient a pharmaceutically effective amount of a compound represented by the formula

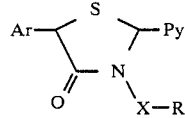

wherein Ar is a phenyl group unsubstituted or substituted with one or more halogen atoms or with one or more $C_1$–$C_4$ alkoxy groups, Py is 3-pyridyl; X—R is $C_1$–$C_4$ alkyl, $C_3$–$C_4$ alkenyl, $C_3$–$C_4$ alkynyl, phenylethyl which is unsubstituted, or substituted with one or more $C_1$–$C_4$ alkoxy groups, ($C_2$–$C_4$) alkanonyloxy ($C_2$–$C_4$) alkyl, or di($C_1$–$C_4$) alkyl amino ($C_2$–$C_4$) alkyl group and the acid addition salts thereof, and at least one pharmaceutically acceptable inert carrier or diluent.

* * * * *